(12) United States Patent
Müller et al.

(10) Patent No.: US 8,128,797 B2
(45) Date of Patent: Mar. 6, 2012

(54) MICROFLUIDIC SYSTEM AND CORRESPONDING OPERATING METHOD

(75) Inventors: Torsten Müller, Berlin (DE); Thomas Schnelle, Berlin (DE)

(73) Assignee: PerkinElmer Cellular Technologies Germany GmbH, Hamburg (DE)

( * ) Notice: Subject to any disclaimer, the term of this patent is extended or adjusted under 35 U.S.C. 154(b) by 775 days.

(21) Appl. No.: 12/161,267

(22) PCT Filed: Jan. 17, 2007

(86) PCT No.: PCT/EP2007/000389
§ 371 (c)(1),
(2), (4) Date: Aug. 29, 2008

(87) PCT Pub. No.: WO2007/082737
PCT Pub. Date: Jul. 26, 2007

(65) Prior Publication Data
US 2011/0083961 A1    Apr. 14, 2011

(30) Foreign Application Priority Data

Jan. 18, 2006  (DE) ..................... 20 2006 010 646 U
Jul. 21, 2006  (DE) ......................... 10 2006 033 889

(51) Int. Cl.
*B03C 5/02* (2006.01)
(52) U.S. Cl. ......... 204/547; 204/450; 204/600; 204/643
(58) Field of Classification Search .................. 204/450, 204/457, 643–645
See application file for complete search history.

(56) References Cited

U.S. PATENT DOCUMENTS

| | | |
|---|---|---|
| 5,948,328 A | 9/1999 | Fiedler et al. |
| 7,208,077 B1 | 4/2007 | Albers et al. |
| 2002/0182627 A1 | 12/2002 | Wang et al. |
| 2003/0104588 A1 | 6/2003 | Orwar et al. |
| 2007/0151855 A1 | 7/2007 | Schnelle et al. |

FOREIGN PATENT DOCUMENTS

| | | |
|---|---|---|
| DE | 4434883 A1 | 8/1995 |
| WO | 0062048 A2 | 10/2000 |
| WO | 2004074814 A2 | 9/2004 |
| WO | 2005075958 A1 | 8/2005 |

OTHER PUBLICATIONS

Fuhr et al., "Levitation, holding and rotation of cells within traps made by high-frequency fields", Biochimica et Biophysica Acta, 1108 (1992), pp. 215-223.
Muller et al., "A 3-D microelectrode system for handling and caging single cells and particles", Biosensors & Bioelectronics 14 (1999), pp. 247-256.
International Search Report for PCT/EP2007/000389.

*Primary Examiner* — Jeffrey T Barton
*Assistant Examiner* — Maris R Kessel
(74) *Attorney, Agent, or Firm* — Caesar, Rivise, Bernstein, Cohen & Pokotilow, Ltd.

(57) ABSTRACT

The invention relates to an operating method for a microfluidic system, including the following steps: feeding of a carrier flow with particles (5) of a first particle type suspended therein into the microfluidic system; charging of a plurality of electrical field cages (1', 1") in the microfluidic system with the supplied particles (5) of the first particle type; the supplying of a carrier flow with particles (6) of a second particle type suspended therein into the microfluidic system; and charging the field cages (1', 1") in the microfluidic system with the supplied particles (6) of the second particle type in such a manner that a particle (5) of the first particle type and a particle (6) of the second particle type is present in at least one of the field cages (1', 1'). The invention also relates to a corresponding microfluidic system.

35 Claims, 11 Drawing Sheets

MICROFLUIDIC SYSTEM AND CORRESPONDING OPERATING METHOD

BACKGROUND OF THE INVENTION

The invention relates to an operating method for a microfluidic system and a correspondingly designed microfluidic system.

Microfluidic systems with dielectrophoretic electrode arrangements for manipulating suspended particles are known, for example, from Müller, T. et al.: "A 3D-Microelectrode for handling and caging single cells and particles", Biosensors and Bioelectronics 14, 247-256 (1999). The dielectrophoretic electrode arrangements can be, for example field cages ("cages") for fixing the suspended particle. The conventional microfluidic systems allow a calculated examination of suspended particles in that they are washed into the microfluidic system and fixed there in a field cage. In the fixed state the suspended particles can then be examined, for example, by impedance spectroscopy or optically.

The previously described known microfluidic systems have the disadvantage that the particles of interest each can only be examined individually. On the other hand, it is often desirable to examine the chemical or biochemical interaction between different particles, which is only possible with great expense with the conventional microfluidic systems. For example, there is an interest in examining the differentiation of stem cells or immune cells in dependency on a certain cell stimulation by chemical or biochemical trigger substances. A further example is the examining of cell-cell interactions.

The invention is therefore based on the problem of improving the known microfluidic systems in such a manner that even the interaction of different particles can be examined. Furthermore, the invention is based on the problem of providing a corresponding operating method for a microfluidic system.

This problem is solved by a microfluidic system in accordance with the invention and by a corresponding operating method in accordance with the invention.

SUMMARY OF THE INVENTION

The invention comprises the general technical teaching of charging the field cages in a microfluidic system successively with particles of different particle types so that particles of different particle types are subsequently present in at least one of the field cages, which allows a particle-specific interaction of the different particle types.

On the one hand, the invention allows therewith a calculated examination of the interaction between different particles with which the field cages are charged, which is interesting, for example, in pharmaceutical research. In this manner a plurality of particle-particle interactions can be studied in order, for example, to determine pharmacologically effective substances.

On the other hand, the invention allows a calculated stimulation of particles with certain trigger substances in order to initiate a reaction which is interesting, for example, in the stem cell research. For example, stem cells can be exposed to certain trigger substances in the field cages in order to achieve and observe a certain cell differentiation.

The individual field cages are preferably selectively charged with the particles of a first particle type by electrically controlling the individual field cages in a selective manner during charging.

The selective electrical control of the individual field cages can have a repulsive effect here so that the field cages concerned reject the washed-in particles and as a result prevent the charging of the concerned field cages with the respective particle. However, there is also the alternative possibility that the selective control of the field cages takes place in such a manner that the concerned field cages fix the respective particles. It is advantageous here that the control of the individual field cages can take place independently of each other so that certain field cages can be calculatedly charged with the desired particles.

Furthermore, there is the possibility that the field cages are controlled in such a manner for charging with the particles of the first particle type that flow vortexes are produced that transport the particles of the first particle type into the field cages.

After the charging of the field cages with the suspended particles the suspended particles adhere preferably in the respective field cages, that is, the particles adhere in the field cage so that the adhering particles are no longer washed out independently of the electrical control of the respective field cage.

The concept of adhesion is used here in a generalized sense and comprises the actual adhesion as active process of living cells as well as the passive adhering, that can occur in the case of living cells as well as of other particles.

However, the adhering of the particles in the field cages is not obligatorily necessary in the scope of the invention but rather it is also possibly sufficient if the suspended particles are held in the respective field cage slightly above the channel wall of the carrier flow channel by means of negative dielectrophoresis.

The particles adhered in the field cages can then be detached again by introducing a surface-dissolving substance into the microfluidic system. The surface-dissolving substance for detaching the adhered particles can have, for example, an enzymatic effect. Examples of such surface-dissolving substances are trypsin, versene, accumax, accutase or chelating agents, in particular EDTA (ethylenediamine tetraacetic acid). It should furthermore be mentioned that the surface-dissolving substance preferably changes the surface tension of the carrier liquid and thereby effects the detaching of the adhered particles. However, the invention is not limited to the previous examples as regards the surface-dissolving substance but rather can also be basically realized with other substances.

The surface-dissolving substance is then preferably washed out of the microfluidic system after a reaction time, while the detached particles are fixed in the field cages by an electrical actuation of the field cages and are therefore not washed out therewith at first.

However, the detaching of the adhered particles can also be achieved by a temperature change of the adhesion surface (e.g., the channel wall of the carrier flow channel), during which the adhesion surface changes its surface properties due to the temperature change, for example, from hydrophilic to hydrophobic or vice versa. The temperature change of the adhesion surface can be effected by, for example, by a heating (e.g., a resistance heating) or a cooling device (e.g., by means of Peltier elements) integrated into the microfluidic system.

The already mentioned charging of the field cages with the particles of the second particle type preferably takes place in that the individual field cages are selectively and electrically controlled during charging in order to either reject or attract the particles.

Alternatively, there is the possibility that the field cages are controlled in such a manner for the charging with the particles of the second particle type that flow vortexes are produced that transport the particles of the second particle type into the field cages.

After the charging of the individual field cages with the particles of the two particle types an examination of a reaction between the particles jointly present in the field cages preferably takes place. This examination can take place, for example, by impedance spectroscopy or optically; however, basically also other examination processes can be used within the scope of the invention.

Then, certain particles in the corresponding field cages can be selected depending on the result of this examination. The selected particles are preferably the particles with which the field cages were first charged. However, it is alternatively also possible that the selected particles are the particles with which the field cages were charged last.

It should be mentioned here that the particles of the different particle types can perform a reaction that can result, for example, in a permanent connection of the particles. If the one particle is a stem cell, this stem cell can experience a certain cell differentiation due to the interaction with the other particle. In such a stem cell differentiation the invention allows a real-time observation and/or real-time examination of the process of the cell differentiation. The selection can then take place in dependency on whether and, if applicable, how the cell differentiation takes place.

The particles selected in this manner can then be removed from the microfluidic system, for example, by flushing out the particles.

It is preferable to use negative dielectrophoresis for the selective charging of the field cages. Thus, negative dielectrophoresis generally has a rejecting effect on the particles depending on the distance from the field cage. However, the particles that are close enough, preferably only one particle, pass into the potential minimum of the field cage, while the other particles experience only the rejecting forces. If the particles, cells are now brought close enough to the channel-/container wall they adhere. Once a cell is adhered, it is stably bound independently of the field and can only be detached by "solvent". A second particle passes preferably under switching off the field to the first particle. If the field remains switched on, the rejecting forces predominate and the second particle does not pass into the field cage.

Thus, the field cages can be controlled in such a manner within the framework of the previously mentioned selective charging of the field cages with the particles that the particles are received by the field cages by means of negative dielectrophoresis. The field cages to be charged are then switched on during the charging while the other field cages can be switched off.

Alternatively, there is also the possibility that the particles are attracted by the field cages by means of positive dielectrophoresis. However, in the case of the planar ring structures preferred in the scope of the invention the particles are deposited on the edge of the annular electrodes. It is therefore advantageous in a fixing of the suspended particles by positive dielectrophoresis if a dot-shaped electrode is arranged inside the annular electrodes, e.g., in the middle of the ring structure.

However, there is also the possibility that the field cages are controlled in such a manner for the selective charging that that suspended particles are selectively rejected by dielectrophoresis by the field cages. The field cages to be charged can then be switched off during charging while the other field cages are switched on and then act in a repulsive manner.

Furthermore, there is the possibility that during the charging of the field cages the field cages to be charged are controlled electrically as well as the field cages that are not to be charged. The field cages to be charged are then controlled in such a manner that the particles are attracted. The other field cages, on the other hand, are repulsively controlled so that the particles are rejected.

Moreover, there is the possibility within the scope of the invention that the individual field cages are controlled with different durations and/or different strengths during the charging with the particles of the second particle type so that a gradient of the particles of the second particle type develops between the field cages. Thus, given a spatially distributed arrangement of a plurality of field cages, almost any desired spatial distributions of the concentration of the particles of the second particle type can be achieved inside the microfluidic system.

Moreover, the invention is not limited to a charging of the individual field cages with particles of two different particle types but rather there is also the possibility within the scope of the invention that the individual field cages can be charged with more than two particles or with particles of more than two particle types. Thus, the charging of the field cages with three different particles allows an examination of the interaction between these three particles.

Furthermore, there is the possibility within the scope of the invention of marking the suspended particles, for example, by a fluorescence marking or by a radioactive marking. This advantageously facilitates the following of the particle reactions or of the particles themselves.

Furthermore, it should be mentioned that the particles of the first particle type as well as the particles of the second particle type can be various particles. Biological cells, stem cells and immune cells can be named by way of example. However, there is also the possibility that the particles are magnetic or magnetizable particles, in particular particles with a magnetic or magnetizable nucleus. Furthermore, even antigens, antibodies, hormones, viruses or viruses modified with genetic engineering can also be considered as particles. Moreover, it is also possible to examine bacteria, so-called latex beads, vesicles or antigen-presenting cells as particles. In general, the particles to be examined within the scope of the invention can also be biological cells, macromolecules, in particular immunoglobulin, particles with an encased target substance in the interior of the particle, e.g., RNA, siRNA, DNA or particles comprising a target structure on their particle surface, in particular in the form of molecules, such as, for example, biological cells, stem cells or nanostructures.

Furthermore, there is the possibility within the scope of the invention that the particles can be 2-phase systems such as, for example, droplets. For example, such 2-phase systems can consist of an aqueous phase and an oil phase, or of an oil phase and a water phase, or of a water phase and a solvent phase, which solvent can be, for example, perfluorotripentylamine (FC70). Furthermore, such a 2-phase system can comprise a gaseous phase and a water phase. In addition, it is possible that a particle consists of several areas/phases (inhomogeneous). For example, a cell could be located in a drop of aqueous medium suspended for its part, for example, in FC70. This system can be used in the combinatorial chemistry and for adjusting defined concentrations (that are different in the array). To this end, for example, at first a drop of an aqueous medium is trapped in a FC70 solution in the field cage and subsequently charged with further droplets with a known size in which a chemical substance (compound) is dissolved in a known concentration. After the fusion the chemical substance is present in a known diluted concentration in the drop that is now trapped. These drops can be released and fused in the chip at another location with a further drop, for example, one containing a cell. This can be used for kinetic examinations, for example, for the determining of IC 50. However, it is especially advantageous if the charging takes place directly in the array and if first particles/aqueous drops with cells are present there.

However, the invention is not limited to the previously mentioned particle types as regards the particles to be used but rather can basically also be realized with other particle types. Furthermore, it should be mentioned that the invention allows an examination of an interaction of any combinations of the previously named particle types.

In one variant of the invention the particles of the first particle type, that are washed in at first, are larger than the particles of the second particle type, that are subsequently washed in. However, it is also possible within the scope of the invention that the particles of the first particle type, that are washed in first, are smaller than the particles of the second particle type, that are subsequently washed in. In addition, there is also the possibility that the particles of the different particle types have the same size.

Furthermore, there is the possibility within the scope of the invention that the particles of the different particle types are moved relative to each other by magnetic forces. For example, the particles of the different particle types can be moved towards each other by the magnetic forces during the charging of the field cages in order that the field cages are charged with particles of different particle types. Furthermore, there is the possibility that the particles of the different particle types are moved away from each other by the magnetic forces during the washing out of the particles from the microfluidic system.

There is the possibility within the scope of the invention that the magnetic forces are adjusted smaller than the dielectrophoretic forces of the field cages during the charging of the field cages so that the dielectrophoretic forces generated by the field cages dominate over the external magnetic forces.

In addition, there is the possibility within the scope of the invention that the magnetic forces are adjusted to be smaller than the bonding forces between the particles of the different particle types during the washing out of the particles from the microfluidic system.

It was already mentioned previously that the interaction of the different particle types is preferably examined in the field cages. For example, this examination can take place by means of measuring electrodes that carry out, for example, an impedance spectroscopic examination.

The suspended particles can be deposited here directly on the measuring electrodes, which is especially advantageous in the so-called patch-clamp technique. To this end the measuring electrodes are preferably adjusted at the frequency of the trapping field to a potential level that corresponds to the potential level that would prevail even without the measuring electrodes at their location. The depositing of the particles to be examined directly on the measuring electrodes offers the advantage that electrical measurements can be carried out in a significantly more sensitive manner.

The measuring electrodes can also be used as manipulation electrodes within the scope of the invention, for example, for particle fusion, cell-cell fusion or for particle poration.

In addition, there is the possibility within the scope of the invention that the field cages are not electrically actuated during the examination, in order to avoid a falsification of the electrical examination by the actuation of the field cages. Therefore, the trapping field is switched off here while the measuring field is switched on.

However, there is also the possibility that the trapping field remains switched on during the measurement. The disturbing influence of the trapping field then has to be suppressed by suitable technical signal processing measures such as, for example, filters or choppers.

In addition, there is also the possibility within the scope of the invention of generating flow vortexes by the electrodes, which vortexes significantly accelerate the flow of the particles to the electrodes. This technique is described in the patent application WO 2005/110605 A1, so that the content of this patent application is to be included in the present description to its full extent. The use of this technique allows that particles can pass from a larger draw-in area into the field cage.

Moreover, it should be mentioned that the invention relates not only to the previously described operating method for a microfluidic system but also to a correspondingly designed microfluidic system itself.

However, the concept of a microfluidic system used in the context of the invention is to be understood in a general manner not limited to microfluidic systems that are integrated on a chip and comprise a closed carrier flow channel as well as feed lines and discharge lines, but rather the concept of a microfluidic system also comprises a flat or bent plate on which at least one field cage is arranged. A further example for a microfluidic system in the sense of the invention is a (micro-)titer plate. The charging of the individual field cages can also take place here by pipetting, so that the carrier flow supply is formed by a pipetting apparatus.

However, the microfluidic system in accordance with the invention preferably provides a carrier flow channel as carrier flow supply via which a carrier flow with particles suspended therein can be supplied. The concept of a carrier flow channel used in the context of the invention is to be understood in a general manner and is not limited to narrow channels with an angular cross section, but rather the carrier flow channel can also have a plane extension so that a plurality of field cages can be arranged in the carrier flow channel in a common plane.

In addition, the microfluidic system comprises several dielectric field cages that are arranged in the carrier flow channel spatially separated from each other and either fix or reject the suspended particles depending on their electrical actuation. By means of a corresponding electrical control of the field cages they can then be selectively charged with the particles of the different particle types.

The individual field cages can be, for example, three-dimensional, as is described in the initially already cited publication of Müller, T. et al.: "A 3D-Microelectrode for handling and caging single cells and particles", so that the content of this publication is to be included to its full extent in the present description as regards the constructive design and the functioning of the field cages. In one exemplary embodiment of the invention the individual field cages can therefore each comprise eight cage electrodes that are cubically arranged.

However, the individual field cages can also be planar, as described in the German patent application 10 2006 002 462, so that the content of this application is also to be included to its full extent in the present description.

In addition, the microfluidic system in accordance with the invention can comprise at least one auxiliary electrode arrangement arranged in the carrier flow channel upstream in front of or downstream behind at least one of the field cages for the fixing or rejecting, respectively of the particles. Such auxiliary electrodes can be, for example, funnel-shaped centering electrodes ("funnel"), deflection electrodes, holding electrodes ("hook") or particle shunts ("switch"), as they are described in the initially described publication of Müller, T. et al.: "A 3D-Microelectrode for handling and caging single cells and particles". The content of this publication is therefore to be included to its full extent in the present description as regards the constructive design and the functioning of the auxiliary electrode arrangement.

In a preferred exemplary embodiment of the invention the individual field cages are arranged on a carrier which is, for example, plate-shaped. The carrier preferably consists substantially of glass, ceramic material, a semiconductor, in particular silicon, or of plastic. However, the invention is not limited as regards the material for the carrier of the field cage to the previously named materials but can also be realized with other materials.

The carrier for the field cages preferably forms boundary surfaces here for the carrier flow channel. For example, the electrodes of the individual field cages can be arranged on the upper or lower channel wall of the carrier flow. However, there is alternatively also the possibility that the electrodes of the field cages are attached on the opposite lateral channel walls of the carrier flow channel and that the spatial orientation data refers to the field of gravity of the earth.

In an exemplary embodiment of the invention the individual field cages are ring-shaped and/or closed, and the field cages can have an attenuation downstream that can consist, for example, of a passivation layer, which in itself is known. The passivation layer then allows the outcoupling of the trapping field for the fixing of the suspended particles, whereas the passivation layer acts in a shielding manner for measuring signals (e.g., direct current measuring signals or low-frequency measuring signals as in patch-clamp measurements or membrane impedance measurements).

Furthermore, there is the possibility within the scope of the invention that the field cages comprise electrodes that are curved against the direction of flow. For example, the electrodes of the field cages can be semicircular or arched with the electrode ends facing against the direction of flow.

The individual field cages are preferably arranged in a matrix form in rows and columns, in which case the individual field cages can preferably be selectively controlled by row control lines and column control lines. Such a matrix-shaped arrangement of a plurality of field cages is described, for example, in the German patent application 10 2006 002 462, so that the content of this patent application is to be included to its full extent in the present description as regards the matrix-shaped arrangement of the field cages.

Furthermore, a preferred exemplary embodiment of the invention provides that the microfluidic system comprises connection contacts that allow a detachable electrical connection of the field cages to a separate driver circuit (generator). For example, such a detachable electrical contacting can be realized by spring contacts.

In a variant of the invention the field cages comprise an outer annular electrode and an inner annular electrode and the outer annular electrode surrounds the inner annular electrode preferably concentrically.

The two annular electrodes can each be planar. There is the possibility here that the planar annular electrodes are arranged in a common electrode plane. However, there is also the alternative possibility that the planar annular electrodes are arranged in electrode planes that are parallel but offset relative to one another.

Furthermore, there is the possibility within the scope of the invention that at least one measuring electrode is arranged inside the inner annular electrode in order to measure the particles fixed in the field cage. However, 2, 3 or even 4 measuring electrodes and/or manipulation electrodes are preferably arranged here inside the inner electrode, which individual measuring electrodes can be selectively round, in particular oval or angular, in particular rectangular.

The arrangement of the measuring electrodes inside the annular electrodes offers the advantage that the dielectrophoretic barrier decreases upwardly and therefore facilitates the trapping of particles from the carrier flow, in particular if the particles are heavier than the carrier liquid, which is typical in the case of biological cells. Moreover, the use of at least one inner electrode allows the process of the trapping and charging in a non-adhered state, which is advantageous for suspension cells such as blood cells. This also works with only one inner electrode (ring-ring-dot structure). If the deposition onto the substrate is required or desirable, it is preferably put on the potential at which the electrode range on average would be even without an inner electrode with connected annular electrodes. Measurements and/or manipulations can then take place between the central electrode and the inner annular electrode. Another advantage of the inner electrode is that both positive as well as negative dielectrophoresis can be used. For the pDEP positioning, e.g., a field with corresponding frequency is connected between the central electrode and the inner and or the outer ring.

Moreover, the annular electrodes can comprise a passivation layer, which passivation layer is preferably designed to be so strong that the passivation layer permits a decoupling of an electrical field for particle fixation, whereas the passivation layer has a shielding effect for direct current signals and low-frequency signals. The fixing of the individual particles in the field cages can be additionally supported by negative pressure. In an exemplary embodiment of the invention the microfluidic system therefore has a low pressure connection that opens into a field cage in order to additionally fix the particles located there.

In an arrangement of measuring electrodes the low pressure connection can also open out between the two measuring electrodes in order to fix the particles there for a measurement.

It should furthermore be mentioned that the measuring electrodes in the field cage can be arranged either symmetrically or asymmetrically.

BRIEF DESCRIPTION OF SEVERAL VIEWS OF THE DRAWINGS

Other advantageous further developments of the invention are explained in detail in the following together with the description of the preferred exemplary embodiments of the invention using the drawings.

DETAILED DESCRIPTION OF PREFERRED EMBODIMENTS

Figure 1A:
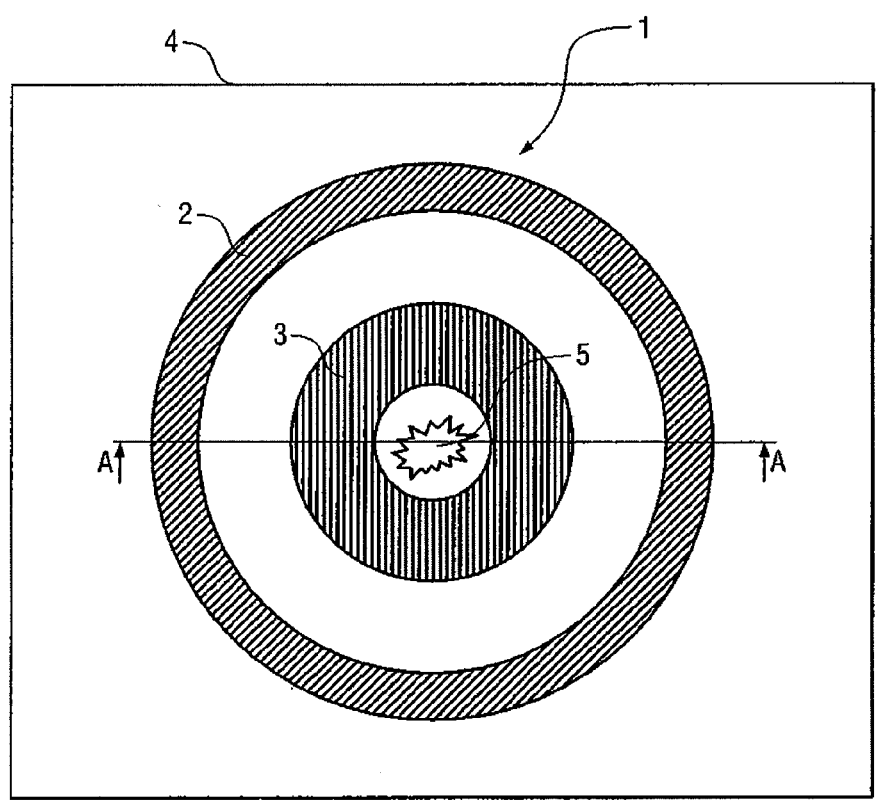
FIG. 1A shows a top view of a field cage of a microfluidic system in accordance with the invention.
Figure 1B:
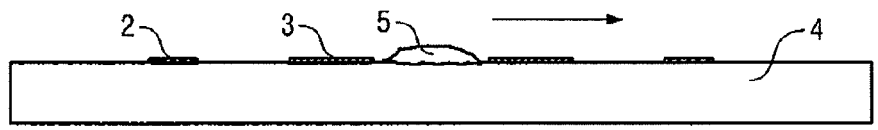
FIG. 1B shows a cross-sectional view through the field cage according to FIG. 1A along the line A-A.

FIGS. 1A and 1B show an exemplary embodiment of a dielectrophoretic field cage 1 that can be used in a microfluidic system in accordance with the invention, as is shown by way of example in the FIGS. 2A and 2B and FIGS. 3A and 3B, respectively.

In this exemplary embodiment the field cage 1 comprises two planar annular electrodes 2, 3 that are arranged in a coplanar manner in a common electrode plane, as is apparent from the cross-sectional view in FIG. 1B. The two annular electrodes 2, 3 are arranged concentrically on a plate-shaped carrier 4 of glass here and can be electrically controlled independently of one another.

A particle 5, that is only schematically shown here, can pass by a suitable electrical control of the two annular electrodes 2, 3 into the field cage 1 by negative dielectrophoresis and be fixed in the field cage 1, and the particle 5 can adhere in the fixed state to the carrier 4 and then also remains adhered to carrier 4 after the field cage 1 has been switched off.

However, the field cage 1 can also be electrically controlled in such a manner that the particle 5 is rejected from the field cage 1 by dielectrophoresis, as a result of which a charging of the field cage 1 with particle 5 and thus also an adhering of the particle 5 inside the inner annular electrode 3 is prevented. A selective control of the field cage 1 therefore allows in the microfluidic system in accordance with the invention and described below to selectively charge the field cage 1 with the particle 5 or to reject the particle 5 in order to prevent a charging of the field cage 1 with the particle 5.

Figure 2A:
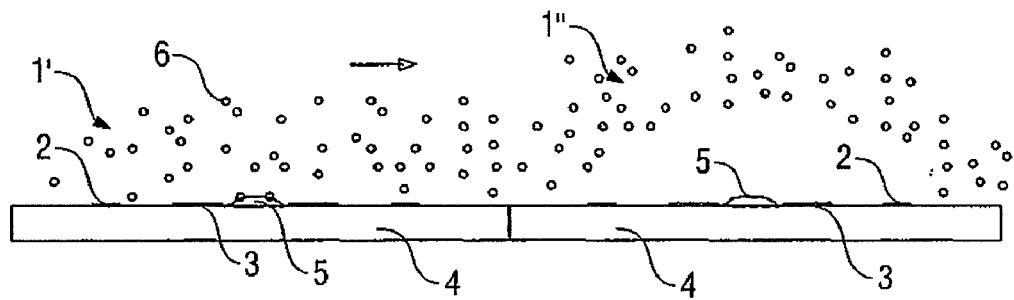
FIG. 2A shows a microfluidic system in accordance with the invention with several field cages during a selective charging with particles in which the one field cage is charged with particles while the other field cage rejects the washed-in particles.
Figure 2B:
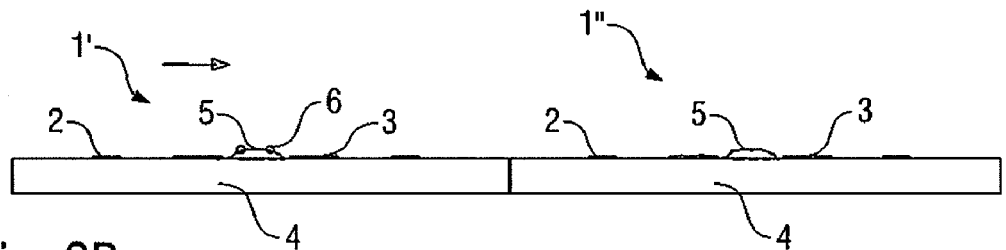
FIG. 2B shows the microfluidic system according to FIG. 2A after the charging of the field cages.

The FIGS. 2A and 2B show partial views of a microfluidic system in accordance with the invention with a plurality of field cages 1', 1" in accordance with FIGS. 1A and 1B. Only two of the field cages 1', 1" are shown in the drawings for the sake of simplification.

Above the carrier 4 here runs a carrier flow channel through which a carrier flow with particles 6 suspended therein flows in the direction of the arrow.

FIG. 2A here shows a state of the microfluidic system in which the particles 5 are already fixed in the two field cages 1' and 1" and adhere there to the carrier 4.

In this state the field cage 1' is switched off so that the particles 6 accumulate on the particles 5.

On the other hand the right field cage 1" is electrically actuated in such a manner in this state that it rejects the particles 6 by dielectrophoresis in order to prevent an accumulation of the particles 6 on the particles 5.

The two particles, 5, 6 belong here to different particle types. Thus, the particle 5 is a biological cell in this exemplary embodiment whereas the particles 6 are viruses that affect the particles 5.

Then, FIG. 2B shows the state in which the two field cages 1', 1" are switched off. The particles 5 then remain adhered to the carrier 4 and can be loosened with a surface-dissolving substance such as, for example, trypsin and washed out of the microfluidic system later.

In the state according to FIG. 2B then an examination of the particles 5 with the particles 6 accumulated there takes place in order to examine the interaction between the particles 5, 6. Certain particles 5 can then be selectively washed out and used further depending on the result of the examination.

Figure 3A:
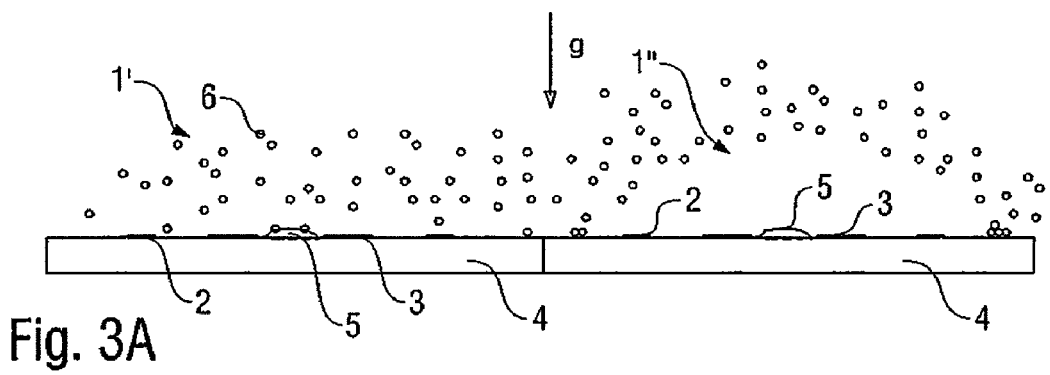
FIG. 3A shows an alternative exemplary embodiment of a microfluidic system in accordance with the invention in which the charging of the field cages takes place from above.
Figure 3B:
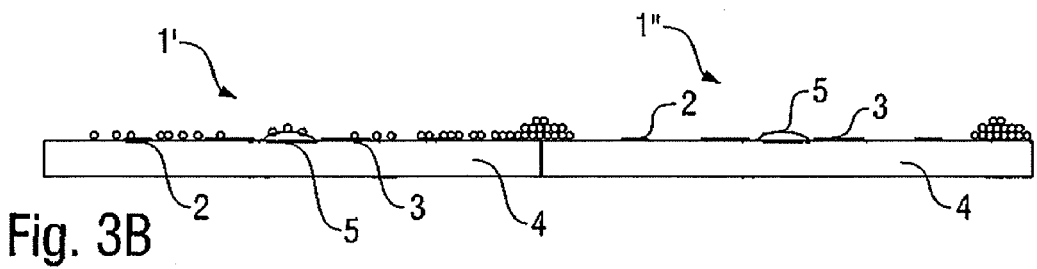
FIG. 3B shows the microfluidic system according to FIG. 3B after the charging.

The FIGS. 3A and 3B show an alternative exemplary embodiment of a microfluidic system in accordance with the invention that largely corresponds with the previously described exemplary embodiment shown in the FIGS. 2A and 2B, so that in order to avoid repetitions reference is made to the previous description and the same reference numerals are used for corresponding parts.

A particularity of this exemplary embodiment consists in the fact that the charging of the field cages 1' and 1" does not take place here parallel to the electrode plane, that is, parallel to the carrier 4, but rather at a right angle to it parallel to the force of gravity, which is illustrated by the sketched-in direction of the force of gravity g.

In the state according to FIG. 3A the field cage 1' is switched off, whereas the field cage 1" is switched on and rejects the particles 6 by negative dielectrophoresis, which prevents an accumulation of the particles 6 in the field cage 1", whereas the particles 6 readily accumulate in the left field cage 1'.

FIG. 3B shows a state of the microfluidic system in accordance with the invention after the charging, when the two field cages 1' and 1" are switched off. A plurality of the particles 6 has then been accumulated in the area of the previously switched-off field cage 1', which also applies in particular for the interior of the field cage 1', where the particles 5, 6 are directly adjacent to each other, so that their interaction can be examined.

In contrast thereto, in the previously connected field cage 1" none of the particles 6 have accumulated on the particle 5 due to the rejecting effect of the field cage 1".

Therefore, the individual particles 5 can be brought together with certain particles 6 in a calculated manner by a selective actuation of the individual field cages 1' and 1" in order to examine their interaction.

Figure 4A:
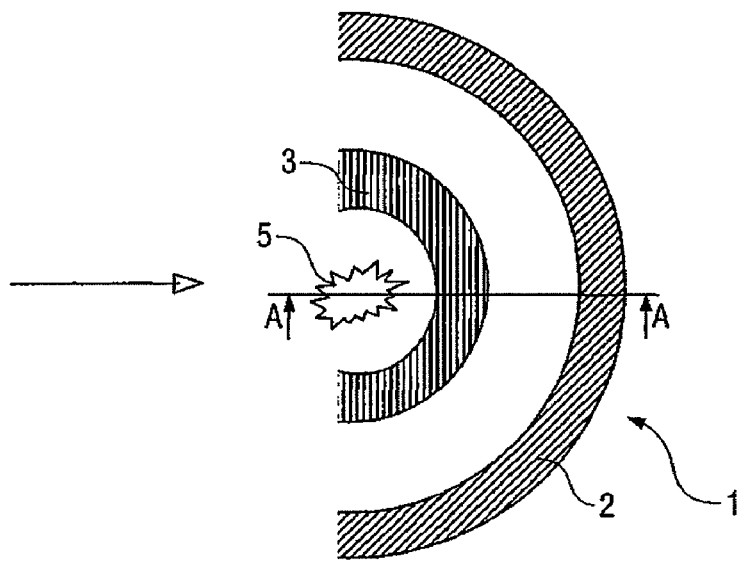
FIG. 4A shows an alternative exemplary embodiment of a field cage for use in a microfluidic system in accordance with the invention.
Figure 4B:
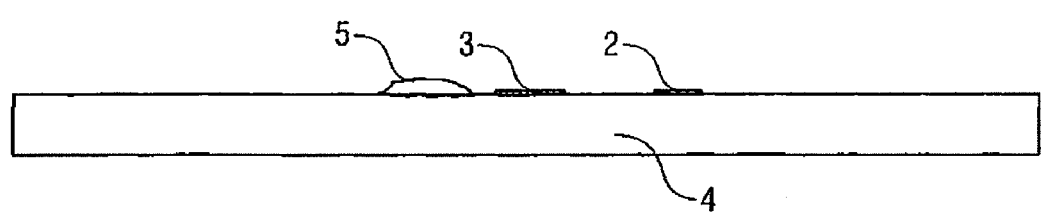
FIG. 4B shows a cross-sectional view of the field cage according to FIG. 4A along the line A-A.

The FIGS. 4A and 4B show an alternative exemplary embodiment of a field cage for use in the microfluidic system in accordance with the invention. This exemplary embodiment partially corresponds with the previously described exemplary embodiment of a field cage shown in the FIGS. 1A and 1B, so that in order to avoid repetitions reference is made to the previous description and the same reference numerals are used for corresponding components.

A particularity of this exemplary embodiment consists in that the annular electrodes 2, 3 are not closed in a ring shape but rather are only semicircular, which two semicircular annular electrodes 2, 3 are curved against the direction of flow.

Figure 5:
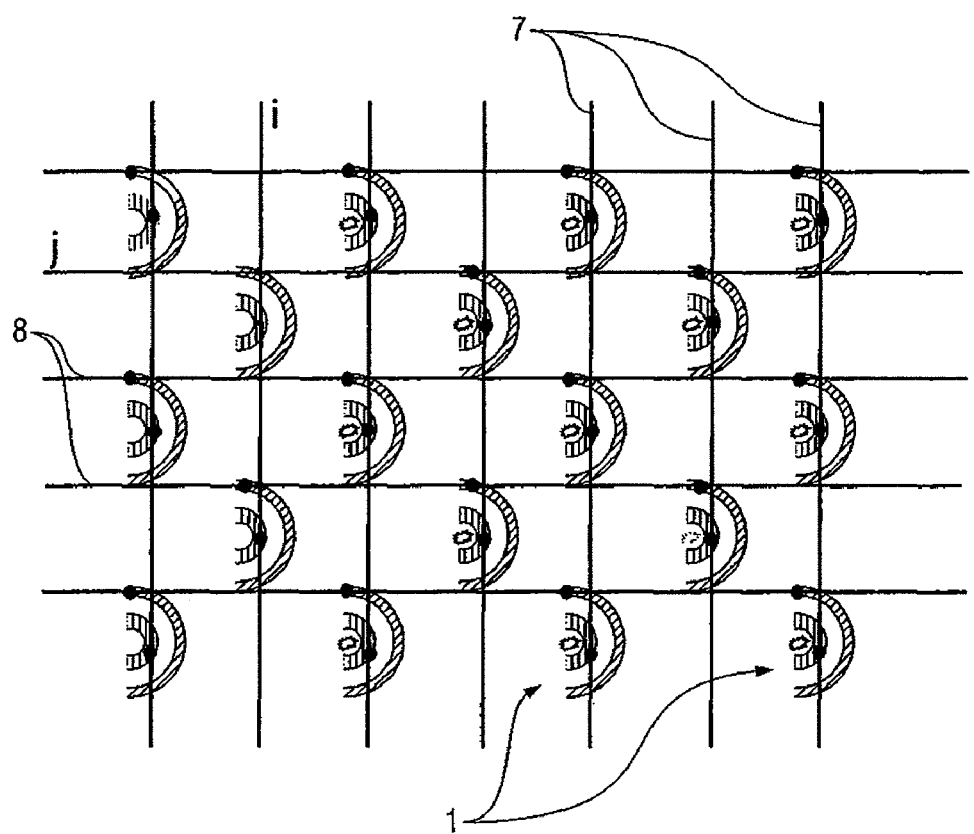
FIG. 5 shows a matrix-shaped arrangement of a plurality of field cages in a microfluidic system in accordance with the invention.

FIG. 5 shows a matrix-shaped arrangement of a plurality of the field cages 1 according to the FIGS. 4A and 4B in which the individual field cages 1 can be selectively controlled by a plurality of column control lines 7 and a plurality of row control lines 8. The column control lines 7 are each connected here to the inner annular electrode 3 of the field cages 1 of the respective column whereas the row control lines 8 are each connected to the outer annular electrodes 2 of the field cages 1 of the respective row. By a suitable controlling of the individual field cages 1 they can be selectively charged with the particles 5, 6 in that the individual field cages 1 are each controlled in a repulsive or a fixing manner or switched off.

For the initial charging of the array according to FIG. 5 with cells, for example, the following procedure is used. Cells are flushed in from the left by a flow. At first, the column control line 7 and the row control lines 8 are grounded except for the column control lines 6 with the indexes imax and imax-1. After filling of the field cages 1 of the columns (imax) and (imax-1) (either under observation or after a sufficiently long time) the next two columns (imax-2) and (imax-3) are subsequently filled by additional activation of the column control lines 7 with the indexes (imax-2) and (imax-3). This process can be continued column by column until the complete filling of the array and has the advantage that the structures located upstream do not hinder the charging of the ones located downstream. The charging with the second particles takes place by means of flow from the right, during which all column- and row control lines 7, 8 are activated (e.g., in phase opposition) except for the ones with cells to be charged (1, M). The column- and row control lines 6, 7 (1, M) are grounded. The optional detaching of target cells takes place by an analogous control by means of a flow via a transverse channel. It is especially advantageous if the base electrode structure was produced as in FIG. 1 but was provided on half its side with a passivation layer dielectrophoretically corresponding at a sufficiently low frequency to the structure according to FIG. 4. The initial charging with cells would then be carried out, for example, with the lower frequency, the calculated charging with triggers and the discharging of the target cells with the higher frequency, during which the cells can then also be released (to or from the left) in the direction of the channel.

Figure 6A:
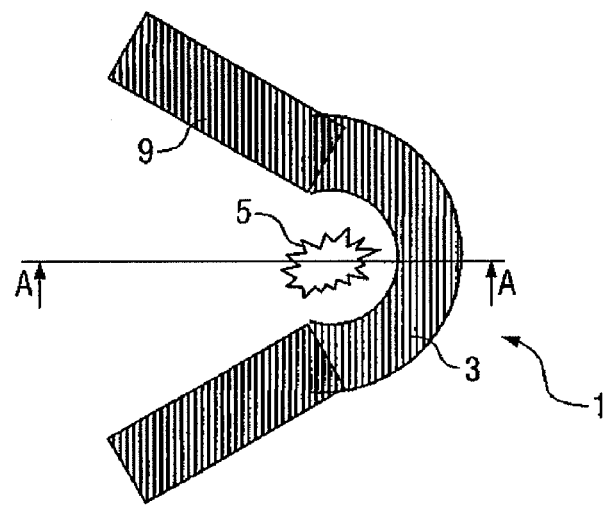
FIG. 6A shows a top view of an alternative embodiment of a field cage for use in a microfluidic system in accordance with the invention.
Figure 6B:
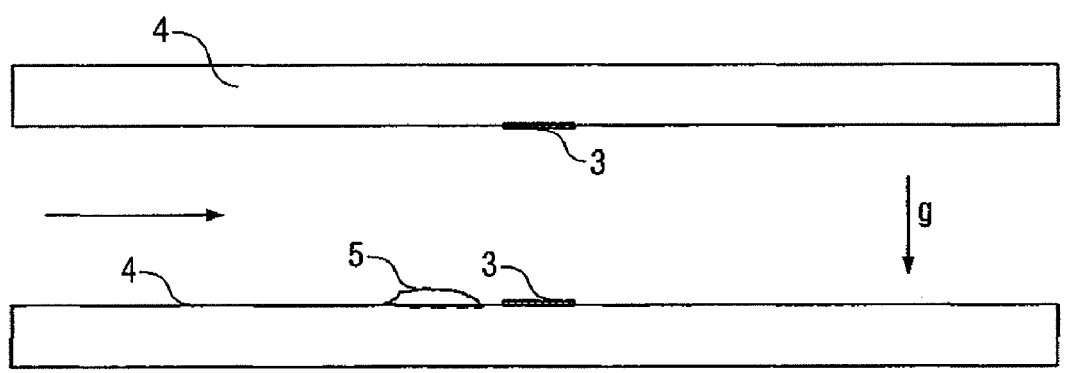
FIG. 6B shows a cross-sectional view of the field cage according to FIG. 6A along the line A-A.

The FIGS. 6A and 6B show an alternative exemplary embodiment of a field cage 1 for use in a microfluidic system in accordance with the invention. This exemplary embodiment partially corresponds with the previously described exemplary embodiment shown in FIGS. 1A and 1B, so that in order to avoid repetitions reference is made to the previous description and the same reference numerals are used for corresponding parts.

A particularity of this exemplary embodiment is that the field cage 1 does not comprise the outer annular electrode 2, as is the case in the exemplary embodiment according to the FIGS. 1A and 1B.

Instead, in this exemplary embodiment field cage 1 comprises a funnel-shaped electrode arrangement 9 ("funnel") upstream in front of the field cage 1 through which the particles 5 are conducted calculatedly into the field cage 1.

Another particularity of this exemplary embodiment is that the inner annular electrode 3 is not closed but rather is open on its side located upstream and merges into the funnel-shaped electrode arrangement 9.

Figure 7A:
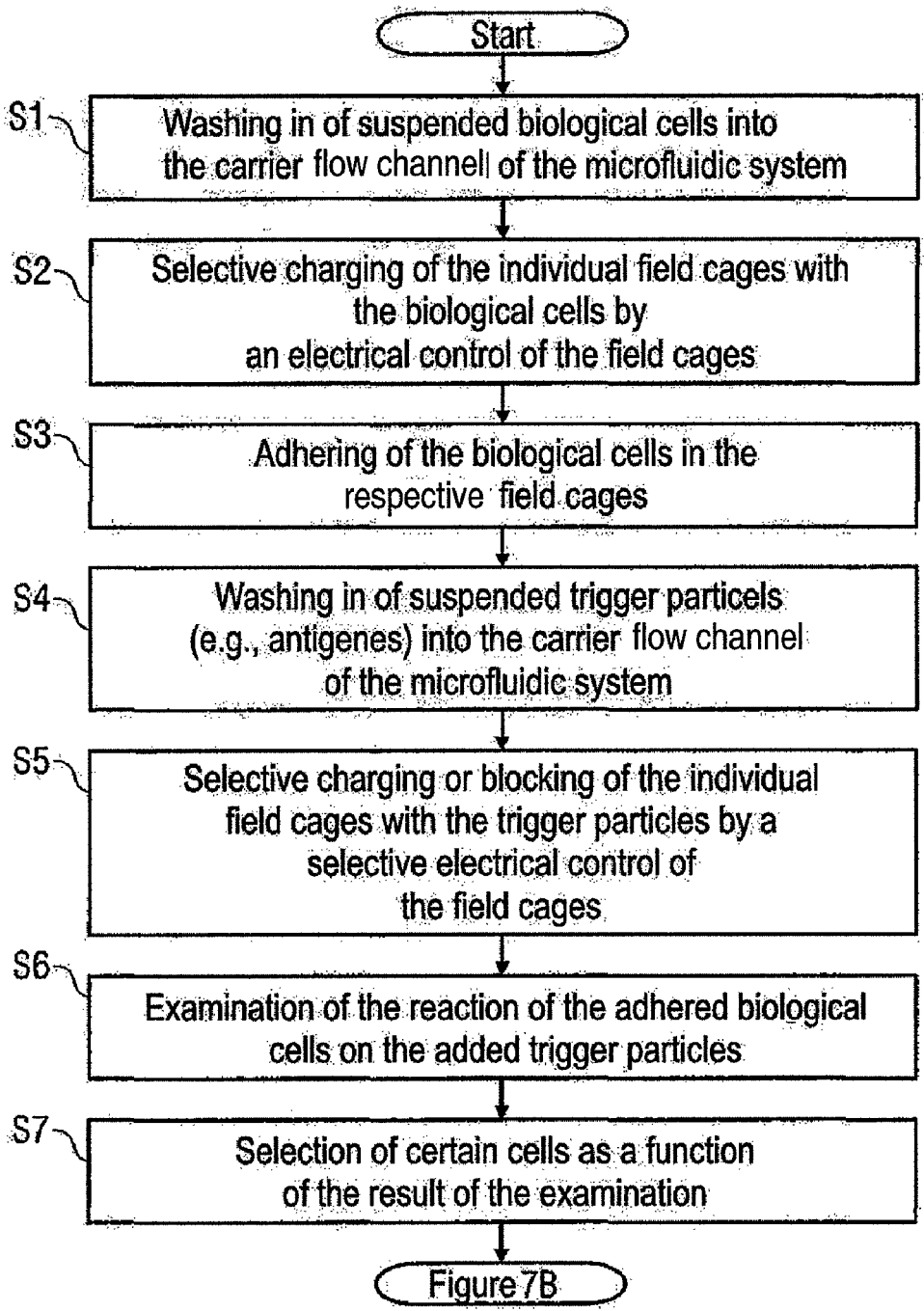
FIG. 7A, 7B show the operating method in accordance with the invention for a microfluidic system in the form of a flowchart.
Figure 7B:
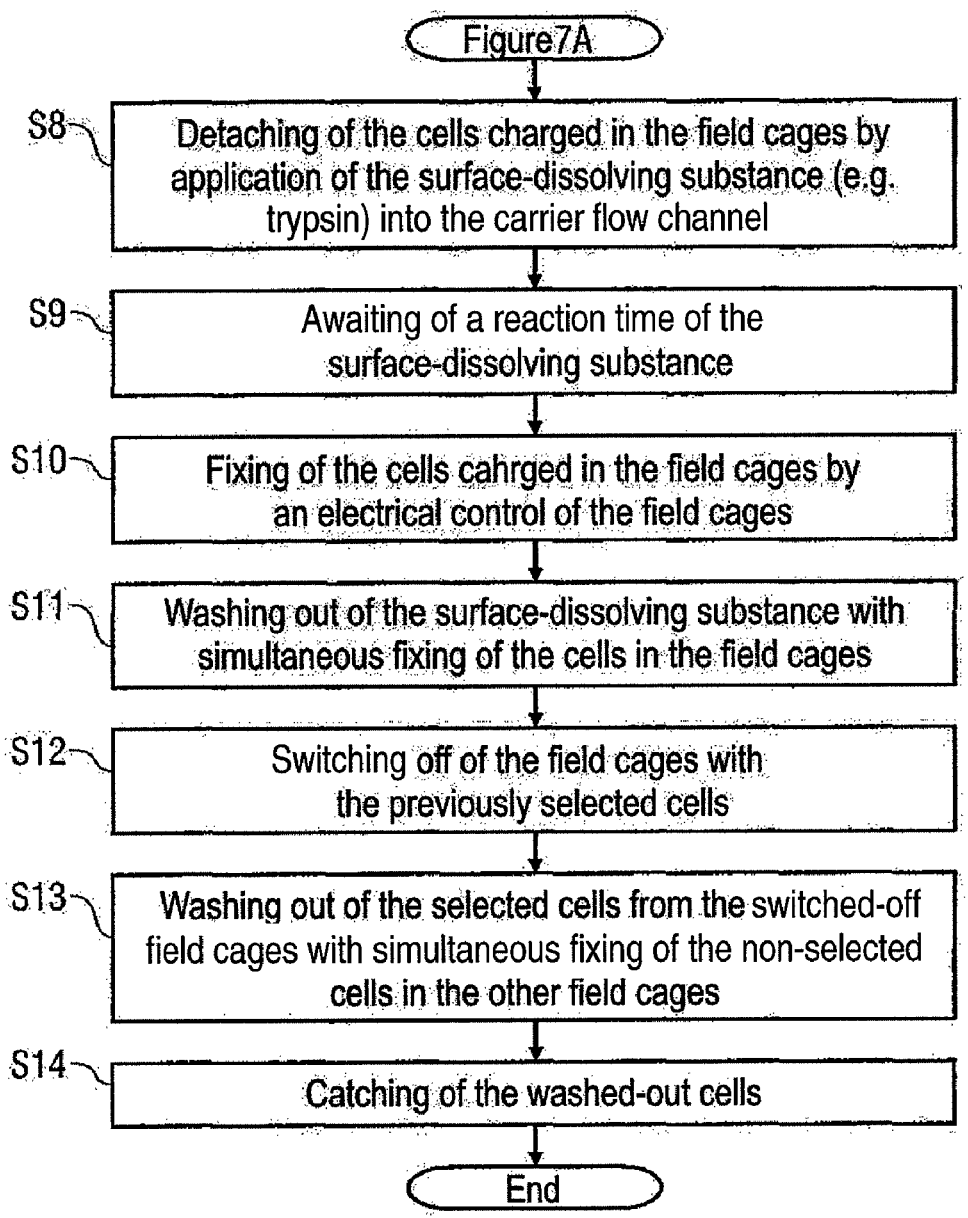

The course of the operating method in accordance with the invention is described in the following using the flow chart in accordance with FIGS. 7A and 7B.

In a first step S1 at first a carrier flow with biological cells suspended therein is washed into the microfluidic system.

In a further step S2 the individual field cages in the microfluidic system are then charged with the flushed-in cells in that the individual field cages are selectively controlled. For this purpose the field cages to be charged with the washed-in cells are controlled in such a manner that the washed-in cells are fixed by negative dielectrophoresis. Whereas, the other field cages, that are not to be charged with the washed-in biological cells, are electrically controlled in such a manner that the washed-in biological cells are rejected by negative dielectrophoresis.

However, it is alternatively also possible that for the particle charging only those field cages are switched on and controlled by negative dielectrophoresis that are supposed to fix the particles, whereas the other field cages remain switched off.

In a further step S3 the biological cells then adhere in the previously selectively charged field cages so that the adhered cells do not become loose even after a subsequent turning off of the individual field cages but rather remain in the charged field cages.

In a further step S4 trigger particles (e.g. antigens) are then washed into the carrier flow channel of the microfluidic system.

The field cages are then charged in a further step S5 in a selective manner with the trigger particles, which is effected by an correspondingly selective electrical actuation of the field cages by means of positive or negative dielectrophoresis. In this manner the individual field cages are charged with biological cells as well as with trigger particles, wherein the interaction between the first supplied cells and the subsequently supplied trigger particles is examined in a further step S6 which can take place, for example, optically or by impedance spectroscopy. However, the examination can also take place by a patch-clamp measurement or by a direct current measurement.

In a further step S7 certain cells are then selected in dependency on the examination of the interaction between the biological cells and the added trigger particles.

Subsequently, in a further step S8 the cells charged in the field cages can then be loosened by application of a surface-dissolving substance (e.g., trypsin), while in a step S9 a sufficient reaction time of the surface-dissolving substance is awaited.

The cells charged in the field cages are then subsequently fixed in the field cages again in a step S10 in order to prevent a washing out of the cells by the carrier flow. For this purpose the field cages are electrically controlled in a suitable manner.

In a further step S11 the previously added surface-dissolving substance is then washed out from the microfluidic system with simultaneous fixing of the cells in the field cages.

After the washing out of the surface-dissolving substance from the microfluidic system, selectively determined field cages containing the previously selected cells are then switched off in a step S12. This selective turning off of the field cages effects that the cells contained therein are washed out from the microfluidic system by the carrier flow in a further step S13 while the other cells remain fixed in the other field cages that continue to be switched on.

In this manner the cells are selectively washed out of the microfluidic system that have previously displayed a certain interaction with the carrier substance.

In a last step S14 the cells selected in this manner and washed out are then caught outside of the microfluidic system for a further use.

It is possible here that the microfluidic system comprises still further channels and that the particles are subjected at first to a manipulation (e.g., a sorting) before the particles are then caught.

Figure 8:
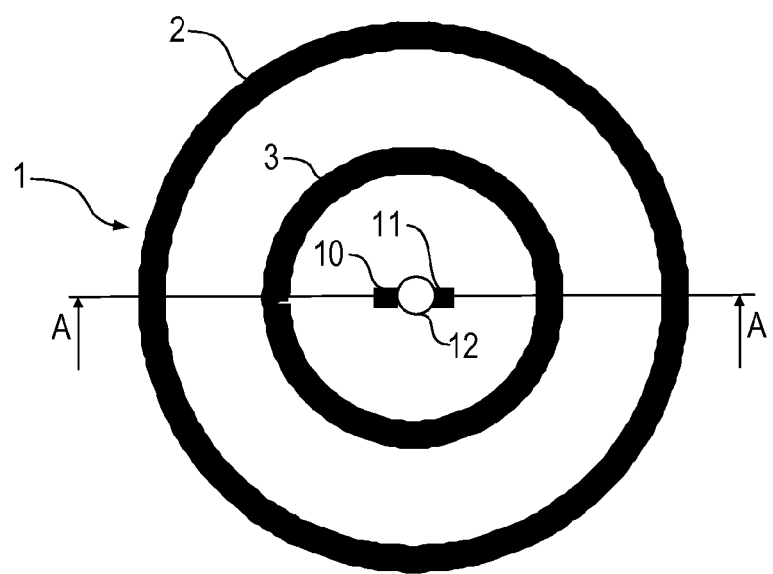
FIG. 8 shows an alternative exemplary embodiment of a field cage in accordance with the invention with coplanar annular electrodes and two measuring electrodes inside the inner annular electrode.

FIG. 8 shows a further exemplary embodiment of a field cage for use in the microfluidic system in accordance with the invention. This exemplary embodiment corresponds largely with the previously described exemplary embodiment shown in the FIGS. 1A and 1B so that that in order to avoid repetitions reference is made to the previous description and the same reference numerals are used for the corresponding parts.

A particularity of this exemplary embodiment is that two measuring electrodes or two manipulation electrodes 10, 11 are arranged inside the inner annular electrode 3 and allow an impedance-spectroscopic examination of the particles 5 and/or 6 adhered inside the inner annular electrode 3.

Furthermore, the manipulation electrodes 10, 11 make a cell fusion possible. To this end, for example, one of the two manipulation electrodes 10, 11 is kept grounded while the other manipulation electrode 10 or 11 is loaded with short impulses of direct current- or alternating current.

The two measuring electrodes 10, 11 are arranged symmetrically on opposite sides of the center point here in the field cage 1.

Furthermore, the field cage 1 comprises a suction opening 12 in the exemplary embodiment via which a low pressure can be generated in the field cage 1 that sucks in the particles 5 and/or 6 and thus supports the charging of the field cage 1 with the particles 5 and/or 6. The suction opening 12 is arranged here between the two measuring electrodes 10, 11 so that the particles 5, 6 are also fixed between the two measuring electrodes 11, 12 during the charging of the field cage 1, which is advantageous for a subsequent measurement.

Figure 9A:
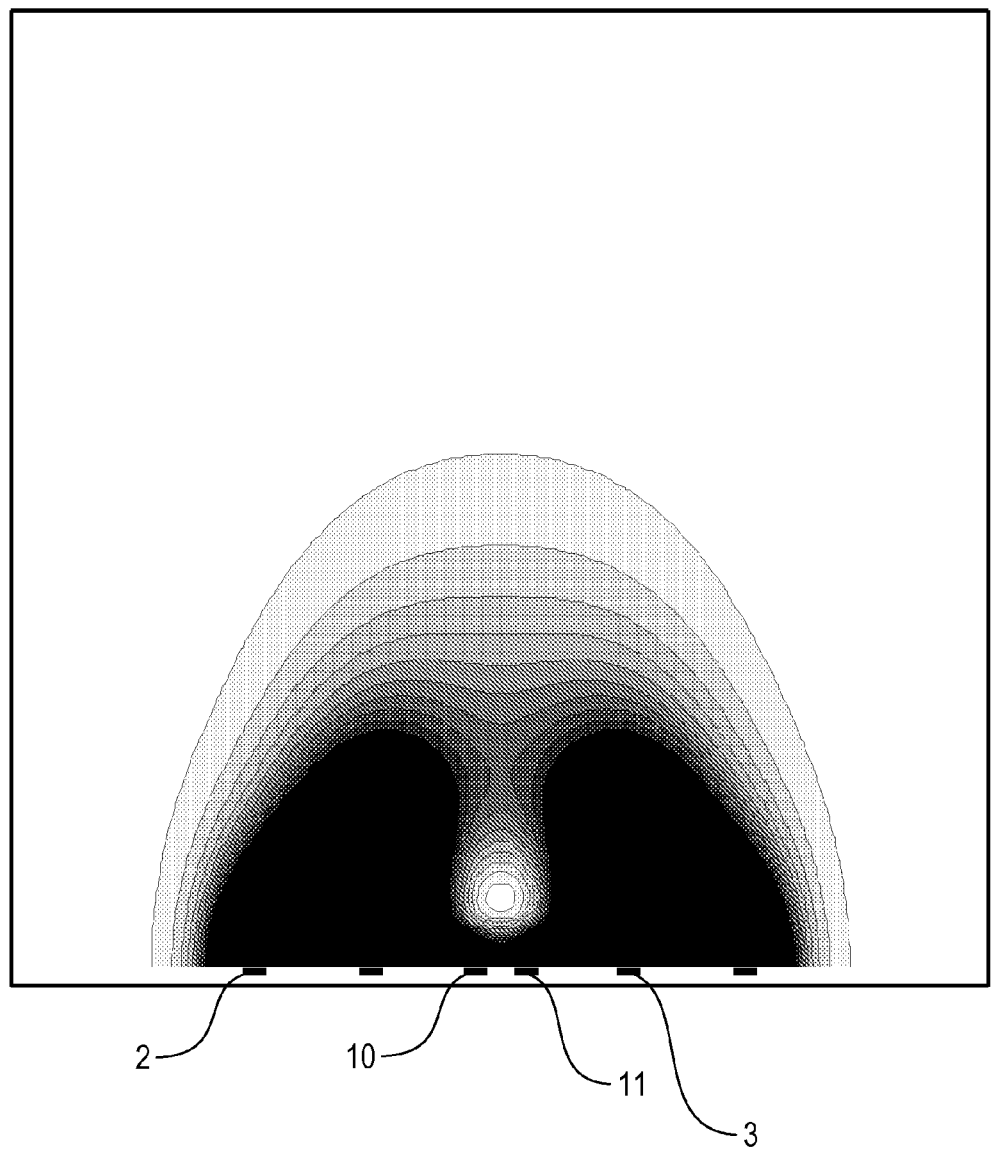
FIG. 9A shows the field distribution $E^2$ in the field cage according to FIG. 8 in the sectional plane A-A, in which the inner annular electrode and the outer annular electrode are controlled in phase opposition with the same voltage while the measuring electrodes are grounded.

FIG. 9A shows the field distribution $E^2$ in the field cage 1 according to FIG. 8, in which the inner annular electrode 3 and outer annular electrode 2 are controlled with phase-opposed electrical signals of the same voltage U whereas the two measuring electrodes 10, 11 are grounded.

Figure 9B:
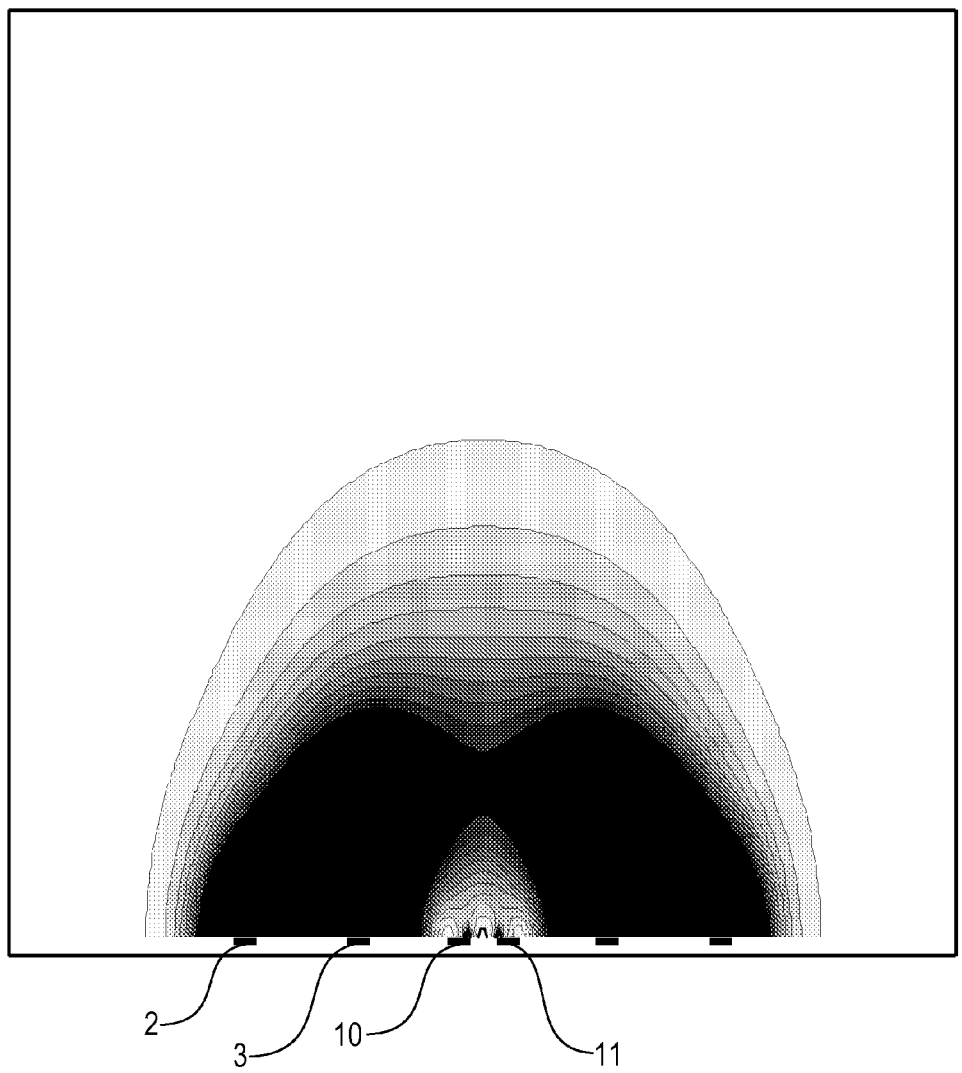
FIG. 9B shows the field distribution $E^2$ in the field cage according to FIG. 8 in the sectional plane A-A, in which the inner annular electrode and the outer annular electrode are controlled in phase opposition with the same voltage while the measuring electrodes are controlled in phase with the inner annular electrode.

FIG. 9B shows the field distribution $E^2$ in the field cage 1 according to FIG. 8, wherein the inner annular electrode 3 and the outer annular electrode 2 are controlled in phase opposition with the same voltage U whereas the two measuring electrodes 10, 11 are controlled in phase with the inner annular electrode 3 with a voltage of 0.26 U.

Figures 10A, 10B, 10C:
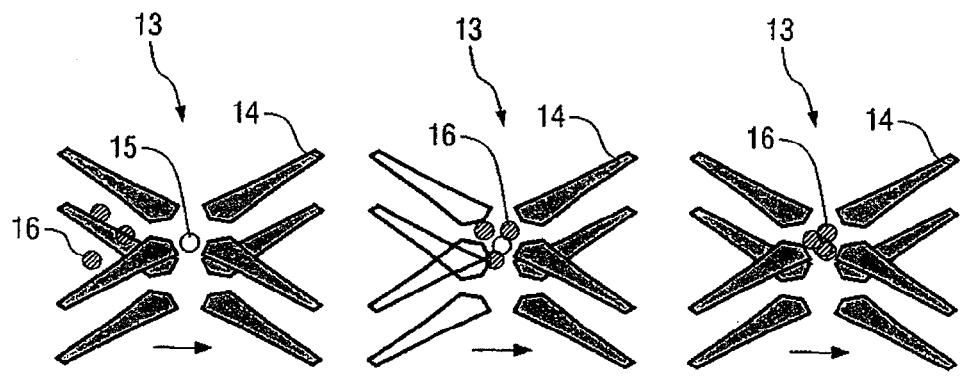
FIGS. 10A-10C show a perspective view of a field cage with eight cage electrodes, with the trapping field being modified for the charging with the particles of the second particle type.

The FIGS. 10A to 10C show an alternative exemplary embodiment of a field cage 13 that is arranged in a microfluidic system in accordance with the invention and onto which a carrier flow flows in the direction of the arrow.

In this exemplary embodiment the field cage 13 comprises eight cage electrodes 14, which cage electrodes 14 are cubically arranged as described, for example in Müller, T. et al.: "A 3D-Microelectrode for handling and caging single cells and particles", Biosensors and Bioelectronics 14, 247-256 (1999).

The cage electrodes 14, whose electrical control is modified, for example, by switching off, attenuation or controlling with changed phase position, are shown without shading whereas the cage electrodes 14 whose control remains unchanged are shown here shaded.

FIG. 10A shows the state here after the charging of the field cage 13 with a particle 15 of a first particle type. In this state the field cage 13 generates a trapping field that fixes the particle 15 in the field cage 13 and keeps further particles 16 of a second particle type outside of the field cage 13.

FIG. 10B shows the charging of the field cage 13 with the particles 16 in that the control of the cage electrodes located upstream is modified in order that the particles 16 can be carried into the field cage 13 by the carrier flow in the direction of the arrow.

Finally, FIG. 10C shows a state in which the different particles 15, 16 are fixed jointly in the field cage 13 by a trapping field in order, for example, to examine the interaction between the particles 15, 16.

Figures 11A, 11B, 11C:
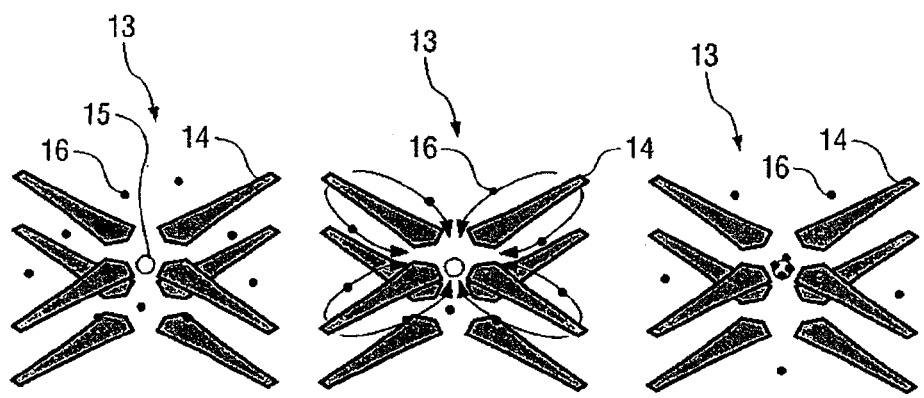
FIGS. 11A-11C show a perspective view of a field cage with eight cage electrodes, with flow vortexes being generated for the charging with the particles of the second particle type.

The FIGS. 11A to 11C show an alternative control of the field cage 13 for charging with the particles 16. For this purpose, the cage electrodes 14 are controlled in such a manner after the charging with the particle 15, shown in FIG. 11A, that vortex flows are generated that run in the direction of the arrow, as is shown in FIG. 11B and described by way of example in WO 2005/110605 A1.

These vortex flows then carry the particles 16 into the field cage 13, where they are finally fixed together with the particle 15 by a conventional trapping field, as is shown in FIG. 11C.

The invention is not limited to the previously described preferred exemplary embodiments but rather a plurality of variants and modifications are possible that also make use of the inventive concept and therefore fall under its protective scope.

LIST OF REFERENCE NUMERALS:

1 field cage
2 annular electrode
3 annular electrode
4 carrier
5 particle
6 particle
7 column control lines
8 row control lines
9 funnel-shaped electrode arrangement
10 measuring electrode
11 measuring electrode
12 suction opening
13 field cage
14 cage electrodes
15 particles
16 particles

The invention claimed is:

1. An operating method for a microfluidic system, comprising the following steps:
 a) supplying of a carrier flow with particles of a first particle type suspended therein into the microfluidic system,
 b) charging of one or more individual electrical field cages in the microfluidic system with supplied particles of the first particle type,
 c) supplying of a carrier flow with particles of a second particle type suspended therein into the microfluidic system,
 d) charging of the one or more individual electrical field cages in the microfluidic system with the supplied particles of the second particle type so that at least one particle of the first particle type and at least one particle of the second particle type is present in the individual electrical field cages e) adhering of the particles of the first particle type in the individual electrical field cages on a channel wall after the charging and before the supplying of the particles of the second particle type.

2. The operating method according to claim 1, wherein the individual electrical field cages are selectively charged with the particles of the first particle type in that the individual electrical field cages are electrically controlled in a selective manner during charging.

3. The operating method according to claim 2, wherein
a) the individual electrical field cages each generate a trapping field in order to fix the particles of the first particle type in the individual electrical field cages, and
b) the trapping field in the individual electrical field cages is modified for the charging with the particles of the first particle type.

4. The operating method according to claim 2, wherein the individual electrical field cages are controlled in such a manner for the charging with the particles of the first particle type that vortex flows carry the particles of the first particle type into the individual electrical field cages.

5. The operating method according to claim 1, further comprising the following step:
detaching of the adhered particles of the first particle type from the individual electrical field cages.

6. The operating method according to claim 5, wherein the adhered particles of the first particle type are detached from the individual electrical field cages by introducing a surface-dissolving substance into the microfluidic system.

7. The operating method according to claim 6, further comprising the following step:
washing out of the surface-dissolving substance from the microfluidic system, during which the particles of the first and second particle types are fixed in the individual electrical field cages by an electrical control of the individual electrical field cages.

8. The operating method according to claim 6, wherein the surface-dissolving substance acts enzymatically.

9. The operating method according to claim 8, wherein the surface-dissolving substance is selected from the group consisting of the following substances:
a) Trypsin,
b) Versene,
c) Accumax,
d) Accutase, and
e) Chelating agents.

10. The operating method according to claim 6, wherein the surface-dissolving substance changes a surface tension.

11. The operating method according to claim 5, wherein the adhered particles of the first particle type in the individual electrical field cages are detached from adhesive surfaces by changing a temperature of the adhesive surfaces, so that surface properties of the adhesive surfaces change.

12. The operating method according to claim 11, wherein the surface properties of the adhesive surfaces change from hydrophilic to hydrophobic or vice versa due to the change in temperature.

13. The operating method according to claim 1, wherein the individual electrical field cages are selectively charged with the particles of the second particle type by electrically controlling the individual electrical field cages in a selective manner during charging.

14. The operating method according to claim 13, wherein
a) the individual electrical field cages each generate a trapping field in order to fix the particles of the second particle type in the individual electrical field cages, and
b) the trapping field in the individual electrical field cages is modified for the charging with the particles of the second particle type.

15. The operating method according to claim 13, wherein the individual electrical field cages are controlled in such a manner for the charging with the particles of the second particle type that vortex flows carry the particles of the second particle type into the individual electrical field cages.

16. The operating method according to claim 1, further comprising the following step:
examining a reaction between the particles of the first and second particle types jointly present in the individual electrical field cages.

17. The operating method according to claim 16, wherein the examining step takes place by one of the following examination processes:
a) Impedance spectroscopy,
b) Direct current measurement,
c) Patch-clamp measurement, or
d) Microscopy.

18. The operating method according to claim 16, further comprising the following step:
selecting certain particles of the first particle type in dependency on the examining step.

19. The operating method according to claim 18, further comprising the following step:
selectively fixing of the certain particles of the first particle type in the individual electrical field cages by electrically controlling the individual electrical field cages in a selective manner.

20. The operating method according to claim 19, further comprising the following step:
removing detached and non-fixed particles of the first particle type from the microfluidic system.

21. The operating method according to claim 1, wherein the individual electrical field cages are electrically and selectively controlled in such a manner for selective charging with the particles of the first particle type and with the particles of the second particle type that the particles of the first and second particle types are selectively rejected from the individual electrical field cages by negative dielectrophoresis and are selectively attracted by the individual electrical field cages by positive dielectrophoresis.

22. The operating method according to claim 1, wherein individual individual electrical field cages are actuated with different durations during charging with the particles of the second particle type so that a gradient of the particles of the second particle type develops between the individual electrical field cages.

23. The operating method according to claim 1, wherein sequentially different particles of the second particle type are supplied with which selectively different individual electrical field cages are charged.

24. The operating method according to claim 1, wherein the particles of the first particle type and the particles of the second particle type are selected from the following group:
a) biological cells,
b) stem cells
c) immune cells
d) magnetic or magnetizable particles,
e) antigens,
f) antibodies,
g) hormones,
h) viruses,
i) bacteria
j) latex beads,
k) vesicles l) antigen-presenting cells,
m) macromolecules,
n) particles with an encased target substance in an interior of the particles,
o) particles comprising a target structure on surfaces thereof,
p) magnetic or magnetizable particles,
q) droplets,
r) 2-phase systems, consisting of an aqueous phase and an oil phase, or of a water phase and an oil phase or of a gaseous phase and a water phase, or of a water phase and a solvent phase.

25. The operating method according to claim 1, wherein the particles of the second particle type are smaller than the particles of the first particle type.

26. The operating method according to claim 1, further comprising the following step:
moving the particles of the first and second particle types relative to each other by magnetic forces.

27. The operating method according to claim 26, wherein the particles of the first and second particle types
a) are moved toward each other during the charging of the individual electrical field cages by the magnetic forces, and/or
b) are moved away from each other during washing out of the particles of the first and second particle types by the magnetic forces.

28. The operating method according to claim 26, wherein
a) the magnetic forces are adjusted smaller than dielectrophoretic forces of the individual electrical field cages during the charging of the individual electrical field cages, and/or
b) the magnetic forces are adjusted to be smaller during washing out of the particles of the first and second particle types than bonding forces between the particles of the first and second particle types.

29. The operating method according to one of the claim 16, wherein the examining step takes place by measuring electrodes, in which the measuring electrodes are adjusted to a potential level that corresponds to a potential level that would prevail even without the measuring electrodes at their location.

30. The operating method according to claim 16, wherein the individual electrical field cages are not electrically actuated during the examining step in order to avoid a falsification of the examining step.

31. The operating method according to claim 1, further comprising the following step:
manipulating the particles of the first and second particle types in the individual electrical field cages by manipulation electrodes.

32. The operating method according to claim 1, wherein
a) the particles of the first and second particle types are stem cells and trigger substances, respectively, in order to trigger a certain cell differentiation, and
b) the cell differentiation of the stem cells takes place in a fixed state in the individual electrical field cages.

33. The operating method according to claim 18, further comprising a step of selectively rejecting the certain particles of the first particle type in the individual electrical field cages by electrically controlling the individual electrical field cages in a selective manner.

34. The operating method according to claim 1, wherein the individual electrical field cages are actuated with different strengths during charging with the particles of the second particle type so that a gradient of the particles of the second particle type develops between the individual electrical field cages.

35. The operating method according to claim 1, wherein the individual electrical field cages are shielded.

* * * * *